US005458905A

United States Patent [19]
Heagle

[11] Patent Number: 5,458,905
[45] Date of Patent: Oct. 17, 1995

[54] AQUEOUS DISPERSION OF SILICONE OIL AND METHOD OF ADDING SILICONE OIL TO A SOLID SUBSTRATE

[75] Inventor: David G. Heagle, Troutman, N.C.

[73] Assignee: Lydall, Inc., Manchester, Conn.

[21] Appl. No.: 82,390

[22] Filed: Jun. 28, 1993

[51] Int. Cl.$^6$ ............ B05D 1/18; B01D 19/00; B01D 37/02
[52] U.S. Cl. ............ 427/2.12; 427/430.1; 427/244; 427/348; 427/352; 427/350; 427/240; 252/321; 252/358; 210/777
[58] Field of Search ............ 604/4, 6; 252/321, 252/358; 210/777, 782, 767; 427/2, 244, 2.12

[56] References Cited

U.S. PATENT DOCUMENTS

| | | | |
|---|---|---|---|
| 4,039,469 | 8/1977 | Raleigh | 252/358 |
| 4,436,647 | 3/1984 | Pirson et al. | 252/358 |
| 4,678,468 | 7/1987 | Hiroyoshi | 623/1 |
| 5,013,717 | 5/1991 | Solomon et al. | 514/56 |
| 5,110,549 | 5/1992 | Gordon | 210/492 |
| 5,258,127 | 11/1993 | Gsell et al. | 210/767 |

FOREIGN PATENT DOCUMENTS

| | | | |
|---|---|---|---|
| 230697 | 4/1959 | Australia | 252/358 |
| WO92/21387 | 12/1992 | WIPO | |

OTHER PUBLICATIONS

H. Bennett, Practical Emulsions, (Chemical Publishing Co., Inc., Brooklyn, N.Y., 1943) pp. 56–79.
Hemocol™ Clinical Data Summary (Revised Jul. 1976), W/C Warner/Chilcott, Division, Warner–Lambert Co. Morris Plains, N.J. 07950.
Whistler, Roy L., Industrial Gums Polysaccharides and Their Derivatives, Second Edition, (Academic Press, N.Y., 1973) pp. 6–7.
Hawley's Condensed Chemical Dictionary, (Van Nostrand Reinhold Co Limited, NY, N.Y, 1987) pp. 19, 224, 225, 472, 581, 931, 932.

Primary Examiner—Richard D. Lovering
Assistant Examiner—Daniel S. Metzmaier
Attorney, Agent, or Firm—Griffin, Butler, Whisenhunt & Kurtossy

[57] ABSTRACT

About 0.01% to 10% of an antifoam silicone oil having a predetermined viscosity of at least about 100 cp is dispersed in an aqueous solution of a water-soluble gum having a viscosity within about 20% of the predetermined viscosity of the silicone oil. A substrate is contacted with the dispersion so as to form a dispersion-wetted substrate and at least a part of the aqueous solution is removed from the substrate, wherein the silicone oil remains in the substrate.

18 Claims, No Drawings

AQUEOUS DISPERSION OF SILICONE OIL AND METHOD OF ADDING SILICONE OIL TO A SOLID SUBSTRATE

The present invention relates to an aqueous dispersion of silicone oil, and particularly to such dispersion which can be applied to solid substrates, such as polymeric substrates, as well as to methods of adding such silicone oil dispersions to such substrates.

BACKGROUND OF THE INVENTION

As is well known in the art, certain silicone oils have considerable antifoaming properties, and such silicone oils are widely used in a variety of environments to control foaming, particularly, of water containing fluids. As an example thereof, silicone oils are used as an antifoaming agent in various apparatus for transporting and cleansing blood. Blood has a high tendency to foam, and any foaming of the blood in such transport and cleansing apparatus considerably disrupts the intended procedures and can cause considerable difficulty when the blood is, even in a lightly-foamed form, again transfused to a patient, for example, in an open heart surgery operation. Foaming of the blood must be reduced or prevented, since foamed blood is life threatening, i.e. can cause air emboli. As another example, silicone oils are used as defoamers in various textile dying processes, where the presence of foamed dye solutions causes non-uniform dying of textiles. Likewise, silicone oils are used in paper-making processes, where, again, foaming causes discontinuity in the paper made by those processes.

Most antifoam silicone oils are not water soluble. While some of the oils are somewhat soluble in very special organic solvents, those solvents do not provide practical solutions of the silicone oils, especially bearing in mind certain properties of those solvents, such as cost, environmental concerns and toxicity. Accordingly, the silicone oils are usually applied in the form of a dispersion, i.e. usually an aqueous and less usually a non-aqueous dispersion. Due to the difficulties of dispersing these silicone oils as an aqueous dispersion, most often, the aqueous dispersions must contain dispersal ingredients which render such aqueous dispersions unsuitable for many applications. For example, a conventional polymeric medical antifoam element is prepared by disposing the silicone oil on a solid substrate form of a polymer. That element may be used in transfer and cleansing devices to prevent foaming of blood. However, medical elements of that nature cannot include any dispersal ingredients which are either harmful to the blood or to the patient, since any such medical element may retain at least some of the dispersal ingredients, and those ingredients can be transferred to the blood.

The general approach in the art for applying such antifoam silicone oils to such medical elements is that of preparing a dispersion of the silicone oil in a fugitive dispersing medium. For example, a dispersion of antifoam silicone oil can be made in trichlorotrifluoroethane (TTE) simply by agitating a mixture of the TTE and silicone oil. A porous polymeric substrate, for example, a polyurethane foam substrate, can then be dipped into that dispersion, and, after removal thereof, the fugitive TTE quickly evaporates from the substrate, leaving only the dispersed silicone oil. This approach, therefore, avoids any possibility of deleterious ingredients remaining in the substrate, and that substrate is, accordingly, quite useful as a medical element for antifoaming in a variety of blood-handling apparatus.

However, regulations now in effect in the United States severely limit the use of chlorinated fluorocarbons, including TTE, and in about 1995 the use of such chlorinated fluorocarbons will be virtually eliminated by those regulations, in order to prevent further ecological damage, i.e. ozone depletion. Therefore, that approach for producing such antifoam substrates will be essentially eliminated by that date. Fugitive dispersing mediums, other than chlorinated fluorocarbons, which have the prerequisite requirements of lack of environmental concerns, toxicity, flammability and the like, are not known. In view thereof, the art has sought other dispersing mediums for the silicone oils.

In this latter regard, a number of different dispersions of silicone oil were previously known in the art. For example, it is known that a siloxane antifoam aqueous emulsion can be prepared with emulsifying agents such as stearyl tartrate, glycerol esters, sorbitan esters of fatty acids, propylene glycol esters, and the like. Since these emulsifiers are food grade emulsifiers, they may be used in human consumable compositions. However, some of these emulsifying agents lead to emulsions of very poor stability and other of the emulsifying agents considerably reduce the antifoaming properties of the dispersion, since these emulsifying agents are foaming agents in themselves. Combinations and variations of such emulsifiers have also been proposed in the art, and U.S. Pat. No. 3,423,340 proposes an aqueous dispersions of a particular siloxane, i.e. benzene-soluble dimethylpolysiloxane and a combination of sorbitan polyoxyethylene monostearate and sorbitan monostearate and/or glycerol monostearate. The emulsion can be further stabilized with thickeners, such as sodium carboxymethyl cellulose.

While such dispersions are acceptable for food compositions which are to be ingested into the body via the alimentary canal, the presence of substantial amounts of emulsifying agents in human blood could cause considerable difficulties, since most emulsifying agents cause substantial damage to blood cells, i.e. hemolysis, and can, therefore, be considered as toxic. Accordingly, compositions, such as the foregoing, cannot be used in producing medical antifoaming elements, as described above.

Somewhat similarly, U.S. Pat. No. 3,650,979 proposed an aqueous dispersion of particular organopolysiloxanes with polyglycol ether or a fatty acid ester thereof or alkyl- or aryl-sulfate or -sulfonate. However, again, these dispersions must include emulsifiers and are not acceptable for the same reasons as in connection with the above-described patent.

Somewhat similarly, U.S. Pat. No. 4,436,647 proposes an emulsion of a very specific organopolysiloxane and a long chain sulfonate ester, such as the sodium salt of stearoyl isethionic acid, thickened with a thickening agent, such as sodium carboxymethyl cellulose, but this composition again, requires substantial amounts of an emulsifier, which renders the composition unsuitable for use in medical antifoam elements.

Other variations of like type emulsions have been described in U.S. Pat. Nos. 3,666,681 and 4,225,456, but, here again, each of these are not suitable for use in medical elements.

Finally, U.S. Pat. No. 4,584,125 proposes a similar dispersion of certain diorganopolysiloxanes with amine compounds, such as aniline, along with a non-aqueous dispersion agent, such as liquid petrolum and a foam destabilizing composition. Here again, this composition is not useful as an antifoam for a medical element, especially in view of the use of liquid petroleum.

As can be seen from the above, the approaches of the prior art are based on, generally speaking, combinations of a silicone oil (sometimes very specific silicone oils), some type of emulsifier, sometimes a thickening agent, such as carboxymethyl cellulose and, of course, water. As noted above, while these dispersions are applicable to a wide range of uses, including food grade uses, they are not applicable to medical substrates, such as a defoaming element in blood handling apparatus. It would, therefore, be of substantial advantage in the art to provide a dispersion of antifoam silicone oils which do not include ingredients unacceptable for application to medical substrates.

SUMMARY OF THE INVENTION

The present invention is based on several primary discoveries and several subsidiary discoveries. As a very important and most fundamental primary discovery, it was found that silicone oils could be formed into a substantially stable aqueous dispersion where the aqueous-dispersing medium has a viscosity similar to the viscosity of the silicone oil being dispersed. As a subsidiary discovery in this regard, it was found that some of the prior art experienced difficulties in dispersing silicone oils in an aqueous-dispersing medium were a result of the physical, rather than chemical, difficulties, i.e. attempting to disperse a high viscosity silicone oil in a relatively low viscosity aqueous-dispersing medium. As a further subsidiary discovery, it was found that if the viscosity of the aqueous-dispersing medium is similar to the viscosity of the particular silicone oil being dispersed, these physical difficulties are overcome, and an adequate dispersion of the silicone oil can be achieved.

As another primary discovery, it was found that to provide adequate antifoam dispersions, the silicone oil must have a viscosity of at least 100 cp, since, below this viscosity, the antifoam properties of the resulting emulsion is less than satisfactory.

As a further primary discovery, it was found that the viscosity of the aqueous-dispersing medium must be within about 20% of the viscosity of the silicone oil. Otherwise, the viscosities are too far removed from each other to provide an acceptable dispersion of the silicone oil.

As another primary discovery, it was found that the viscosity of the aqueous-dispersing medium could be adequately adjusted simply by dissolving a water-soluble gum therein, in amounts sufficient to reach viscosities of the dispersing medium similar to the viscosities of the silicone oil, i.e. within 20% of the viscosity of the silicone oil.

As a subsidiary discovery, it was also found that suitable water-soluble gums include a number of non-toxic biologically acceptable gums which may be used in connection with blood and like body fluids, for example, carboxymethyl cellulose.

As a further very important discovery, it was found that when a solid substrate to which the silicone oil dispersion is to be applied has hydrophobic surfaces, the silicone oil in the dispersion preferentially wets those hydrophobic surfaces, and the aqueous solution of the gum is preferentially excluded from wetting of those surfaces. This results in preferential deposition of the silicone oil on the hydrophobic substrate surfaces and only a loose adherence of the aqueous-dispersing medium on the hydrophobic substrate surfaces. This allows the aqueous-dispersing medium to be easily removed from the substrate, for example, simply by centrifuging or washing of the substrate.

As a further primary discovery in connection with the dispersion and the use thereof as described above, it was found that a wide range of contents of silicone oils could be formed into such a dispersion. The silicone oil may be as little as 0.01% of the dispersion and, by virtue of the preferential wetting, as described above, will still provide substantial amounts of silicone oil being deposited on the substrate. On the other hand, by virtue of the aqueous-dispersing medium being easily removed from the substrate, the amount of silicone oil in the dispersion can be quite large, i.e. up to 10% or greater.

Thus, very briefly stated, the present invention provides an aqueous dispersion of an antifoam silicone oil where the dispersion has 0.01% to 10% of a silicone oil having a predetermined viscosity of at least 100 cp dispersed in an aqueous solution of a water-soluble gum having a viscosity within 20% of the predetermined viscosity of the silicone oil.

Further, the present invention provides a method of adding the antifoam silicone oil to a solid substrate. The method includes mixing a silicone oil having a predetermined viscosity of at least 100 cp with an aqueous solution of a water-soluble gum having a viscosity within 20% of the predetermined viscosity of the silicone oil to form a dispersion of the silicone oil in the aqueous solution. The substrate is then contacted with the dispersion to form a dispersion-wetted substrate. At least a part of the aqueous solution is removed from the substrate such that the silicone oil, largely, remains on the substrate.

DETAILED DESCRIPTION OF PREFERRED EMBODIMENTS OF THE INVENTION

Since, as noted above, the present dispersion depends upon the relative physical properties, i.e. viscosity, of the silicone oil and the aqueous dispersing medium, the particular chemical compositions of the silicone oils and the water-soluble gums are not critical, which is an important advantage over the prior art where the particular silicone oils and emulsifiers can be quite critical. Thus, a wide range of antifoam silicone oils and water-soluble gums may be used, so long as the silicone oils and the solutions of the water-soluble gums give the viscosities, and especially the relative viscosities therebetween, as described above. However, the silicone oil must be in oil form, i.e. in liquid form at room temperature (20° C.) and have a viscosity at room temperature of at least about 100 cp. In this regard, it was found that if the viscosity is substantially below about 100 cp, the silicone oil and the dispersion thereof will not have substantial antifoam properties. On the other hand, the viscosity of the silicone oil can be almost any higher viscosity, so long as that viscosity is consistent with the silicone being in oil form at room temperature, and viscosities up to 50,000 cp are easily used for such dispersion. However, more preferably, the viscosities will be at least 200 or 300 cp, and more preferably at least 400 cp, and generally less than 30,000 cp, and more preferably less than 10,000 cp, and more usually less than 3,000 cp, at room temperature.

Of course, when the dispersion is intended for application to a medical substrate, the silicone oil must be a medical grade antifoam silicone oil. The art is fully familiar with those antifoam silicone oils which are medical grade, but, generally, the medical-grade silicone oils include those which have been tested for, among others, allergenic reactions, essential freedom from impurities and byproducts, as well as processing aides. Medical-grade silicone oils, however, may, in fact, be formulations of silicone oils, e.g. may be formulated to contain other ingredients, such as medically-acceptable stabilizers and the like. Medically-acceptable formulations may also contain very small amounts of finely divided silica, but the amount is so small as to be innocuous to the blood or blood cells. Medical-grade silicone oils are usually manufactured in such forms, for example, Dow Corning Antifoam A-medical-grade silicone oil, which is a very useful silicone oil formulation in the present invention. These added ingredients are, however, only in very small amounts which do not affect basic characteristics of the silicone oil or the resulting dispersion, i.e. the dispersion still consists essentially of the silicone oil and the water-soluble gum solution. Thus, for purposes of the present specification and claims, the term "silicone oil" is intended to include such formulations thereof.

It will also be appreciated that the viscosity of the silicone oil or aqueous solution of the water-soluble gum will show different viscosity values depending upon the particular viscometer used for determination. The different values, of course, are convertible between the different viscometers, but the present viscosities are based on a Brookfield viscometer, and if another viscometer is used, the corresponding values are intended by the present specification and claims.

The water-soluble gum can be almost any water-soluble gum, either natural or synthetic. Natural gums, such as guar gum, agar, carrageen, gum arabic, corn starch, gum karaya, gum tragacanth, locust bean gum, dextran, xantham gum, alginates, and the like, or mixtures thereof, are easily used. Synthetic gums, e.g. water-soluble polymers, such as methyl cellulose, carboxymethyl cellulose, polyvinyl alcohol, polyacrylamides, polyacrylates, cationic resins, polyacrylic acid, polyoxyethylene, polyvinylpyrrolidinone, vinyl ester polymers, and the like, may also be used. The preferred gums are carboxymethyl cellulose and polyacrylates, since those gums have essentially no irritating properties in the body fluids, are easily formed into an aqueous solution and can easily provide a range of viscosities to match the viscosities of the particular silicone oils being dispersed. The amount of the gum used in the solution thereof, will, of course, depend upon the particular gum being used, its particular molecular weight, and the viscosity needed in the aqueous solution thereof, i.e. a silicone oil viscosity matching viscosity. The amount, therefore, will have to be determined by preliminary tests. However, very generally speaking, the amount of gum in the solution will be from about 0.1% to about 10%, and more usually about 1% to about 5%.

Once the solution of the water-soluble gum is prepared at the correct viscosity (measured at room temperature −20° C.), the aqueous dispersion of the silicone oil is prepared simply by mixing the silicone oil into the aqueous solution of the water-soluble gum, with stirring. The amount of silicone oil that can be added to such solutions can vary widely, i.e. from as little as about 0.01% to as much as about 10%. While it would ordinarily seem that a concentration of silicone oil of 0.01% would be far too low to provide substantial antifoaming properties to a substrate, in view of the preferential wetting, described in more detail below, even such small concentrations of silicone oil provide very powerful antifoaming properties to the substrate. On the other hand, since the present dispersion is stable for some length of time, e.g. usually at least 5 minutes and for usually at least 15 minutes or even 30 minutes, without any substantial stirring, high concentrations of silicone oil may be used, i.e. up to about 10%. At higher concentrations, however, the stability of the dispersion decreases, and at concentrations above about 10%, the stability is reduced to less than that considered to be desirable for present purposes, and it is for this reason that the concentration of silicone oil in the dispersion should be 10% or less. Preferably, the amount of silicone oil in the dispersion is between about 0.1% and 8%, especially between about 1% and 5%.

It is critical to forming the present dispersion that the viscosity of the aqueous solution of the water-soluble gum be within at least about 20% of the predetermined viscosity of the silicone oil. If the viscosity of the gum solution is not that closely matched to the viscosity of the silicone oil, then the dispersion will be substantially unstable, and the dispersion will commence to break before practical application times have elapsed. In this regard, a practical application time is considered to be at least 5 minutes, after stirring the silicone oil into the solution, that an adequate dispersion remains. However, the closer the match of the viscosities, the more stable the dispersion, and for this reason, the viscosity of the aqueous solution of water-soluble gum, more preferably, is within at least about 15%, more preferably within at least about 10%, and even more preferably within at least about 5%, of the predetermined viscosity of the silicone oil.

The method for adding the silicone oil to a solid substrate, for antifoam purposes, entails preparing the aqueous dispersion of the silicone oil, as described above, and contacting the desired substrate with that dispersion. In more detail, the silicone oil, having a predetermined viscosity of at least about 100 cp, is mixed with an aqueous solution of the water-soluble gum having a viscosity within about 20% of the predetermined viscosity of the silicone oil, to form the dispersion of the silicone oil in the aqueous solution. The amount of mixing required depends, in part, on the particular silicone oil and aqueous solution of gum, as well as the absolute viscosities of each, and the relative viscosities therebetween. Thus, some experimentation in this regard may be required. However, for almost all dispersions of silicone oil in the aqueous solution of gum, only usual laboratory mixing is required, e.g. with a conventional laboratory stirrer, magnetic stirrer or high speed mixer, such as a Lightening mixer, or other conventional homogenizing equipment, such as the homogenizing equipment used in the dairy industry. It is only necessary to continue the mixing until a stable dispersion is formed, and with usual silicone oils and aqueous solutions of gum, as well as usual mixing equipment, that stable dispersion can be reached in only seconds or a minute or two of mixing, e.g. about 3 seconds to 5 minutes.

After the dispersion of the silicone oil is prepared, the substrate is contacted with the dispersion so as to form a dispersion-wetted substrate. That contacting of the substrate with the dispersion can be by any of the conventional methods of the art, including one or more of immersion of the substrate in the dispersion, padding the substrate with the dispersion, or spraying the substrate with the dispersion.

While any solid substrate may be used, as desired, most often for a medically-acceptable, antifoam element, the substrate is porous. This is because, for example, blood is flowed around and through the substrate to control foaming thereof, for example, in an artificial heart machine used during open heart surgery. The porous substrate allows the blood to pass therethrough and break any foam which may be generated in the artificial heart apparatus. Conventionally, in these applications, the substrate is in the form of an expanded surface substrate, such as a foam, and especially a polymeric foam, such as polyurethane foam. However, for other applications, the substrate can be as desired and could take the form of cellulose foams, olefin polymer foams, etc., a matt of natural or synthetic fibers, particulate material in an enclosure, and the like. Indeed, many applications may be made where the antifoaming is not in connection with any medical apparatus, and, in such cases, of course, none of the silicone oil, water-soluble gum or substrate need be medically acceptable, and, in this connection, other gums, such as water-soluble carboxyvinyls, could be used, along with other substrates, such as diatomaceous earth and the like. However, when the substrate is in the form of an antifoam agent for a blood-handling apparatus, all of the silicone oil, gum and substrate must be medically acceptable, as described above.

After the substrate is contacted with the dispersion, at least a part of the aqueous solution is removed from the substrate such that, with the removal of the aqueous solution, the silicone oil remains in the substrate. Any of the conventional methods for removing the aqueous solution from the substrate is acceptable, such as one or more of centrifuging the substrate, applying a vacuum to the substrate, blowing onto the substrate pressurized gas, e.g. air, displacing the aqueous solution with a water-insoluble fluid, e.g. higher alcohols, and dissolving the aqueous solution in an organic solvent, e.g. lower alcohols. However, more preferably, the aqueous solution is removed from the substrate, either by centrifuging the substrate or simply pressing or squeezing the substrate, e.g. between pressure nip rolls, to remove the aqueous solution and retain the silicone oil. Thus, for example, the so-produced medical element will consist essentially of the substrate, the silicone oil (or composition thereof as explained above) and remaining water-soluble gum solution.

While not necessary for some applications, normally, after removing the aqueous solution, the substrate is dried, e.g. in conventional ovens or on conventional cans, or conventional driers, and usually at temperatures of about 215° F. or less, e.g. 150° F. to 210° F., so as to not substantially cause boiling of the aqueous solution, while drying takes place.

With this process, the add-ons of the silicone oil to the substrate can vary considerably, depending, primarily, on the nature of the substrate itself. However, generally speaking, the amount of silicone oil added to the substrate is between about 0.5% and 50%, and more usually between about 1% and 40%, and especially between about 5% and 35%.

Both the ease of removing the aqueous solution of the water-soluble gum and the retention of silicone oil on the substrate are substantially affective by the properties of the substrate itself, and particularly the surface properties thereof. When the substrate has at least in part hydrophobic surfaces, those hydrophobic surfaces will cause preferential wetting of those surfaces by the dispersed silicone oil and, to a large extent, prevent substantial wetting of those same surfaces by the aqueous solution of the water-soluble gum. As can be easily appreciated, in view thereof, preferential deposition of the silicone oil on the hydrophobic substrate surfaces occurs, and only a light adherence of the aqueous solution on the hydrophobic substrate surfaces occurs. This allows the aqueous solution to be easily removed from the substrate, for example, by the techniques described above, and even by the simple technique of pressing or squeezing the substrate. In addition, when the surfaces are hydrophobic, essentially all of the aqueous solution of the water-soluble gum can be removed by washing of the substrate with water, which will, essentially, remove all of the ingredients of the aqueous solution, without displacing substantial amounts of the silicone oil from the substrate. In the case of a medical substrate, of course, such washing would be with sterilized, or at least demineralized, water. After such washing, then drying, if desired, would take place, as described above.

Hydrophobic surfaces are presented by a number of polymeric compositions, such as polyethylene, polyurethane, nylon, orlon and the like. Accordingly, when a hydrophobic polymer, of that nature, is used as the substrate, either in solid or porous or foamed form, the preferential deposition of the silicone oil and the ability to completely remove the solution of water-soluble gum by washing, as explained above, is easily obtained. Thus, especially for medical elements, a hydrophobic surface, especially of a porous substrate, is greatly preferred.

The invention will now be illustrated by the following examples where all percentages and parts are by weight, unless otherwise indicated, which is also true for the foregoing specification and the following claims.

EXAMPLE 1

7.5 gm of carboxymethyl cellulose (manufactured by Aqualon/Type 7M) was mixed with 300 gm of water by stirring with a conventional laboratory stirrer to yield an aqueous solution having a concentration of about 2.0%. The viscosity was 500 centipoises as measured with a Brookfield viscometer.

15.0 gm silicone oil having a viscosity of about 500 cp (Dow Corning Antifoam A-Medical Grade) was added to the solution with mixing by the same laboratory stirrer to form a dispersion of the silicone in the solution.

A polyurethane foam part fabricated from flat stock which was 0.340 inch thick and had 20 pores per inch was dipped into the dispersion. The excess liquid was squeezed out by rubber-coated pressure rollers. Before dipping, the foam weighed 25 gm. After dipping and squeezing, it weighed 32.9 gm, for an add-on of 7.9 gm or a 32% add-on.

To test the antifoaming properties of the treated foam part, 600 ml water and 20 drops of Triton GR5 (Rohm & Haas) surfactant were added to a 1000 ml jar. When the jar was agitated by hand for 30 seconds, foam filled the jar and was not dissipated for over 10 minutes. The procedure was repeated with a new jar, except a 2.5 inch circle of the treated foam was added to the jar. In this jar, very little foam was generated, and the foam was completely dissipated 10 seconds after the agitation was stopped.

EXAMPLE 2

The procedure of Example 1 was repeated, except that after the dipped and squeezed foam was produced, that treated foam was extracted with trichlorotrifluoroethane (TTE) and then subsequently washed with water. An analysis was performed in regard to the amount of silicone extracted by the TTE and the amount of silicone remaining in the aqueous solution of the water-soluble gum. From the extractant, it was found that 94% of the add-on weight of the silicone oil was removed by the extractant, and the extractant contained only 6% of the water-soluble carboxymethyl cellulose solution. This shows that the silicone oil was considerably preferentially deposited on the hydrophobic surfaces of the foam, as opposed to the carboxymethyl cellulose solution, which is of substantial importance in providing medical substrates.

In this latter regard, since some gums, including carboxymethyl cellulose, can allow microbiological growth, this can result in the pyrogen and bioburden of such treated substrates to, eventually, become relatively high. However, for such medical substrates, this can be easily corrected by washing the treated substrate, as described above, or washing in an ultrasonic bath, with ultrapure water. This washing completely removes any biological matter that may be present, as well as any remaining carboxymethyl cellulose, and provides a medical substrate with antifoam properties which has no pyrogenic or bioburden characteristics.

EXAMPLE 3

To 300 grams of room temperature water were added 25 grams of an aqueous solution of sodium polyacrylate (Alcogum-296W, produced by Alco Chemical Company, Chattanooga, Tenn.—an anionic colloidal solution at 15% solids). After stirring for several minutes with a laboratory stirrer, a solution having a Brookfield viscosity of 430 was produced. To this solution was added 19 grams of silicone oil (Dow Corning Antifoam A-medical grade) having a Brookfield viscosity of 430, with stirring for several minutes with the same laboratory stirrer. A uniform dispersion of the silicone oil in the gum solution was obtained.

The same polyurethane foam part of Example 1 was immersed in the dispersion and excess dispersion was squeezed therefrom by passing the part between pressure nip rolls and dried in a laboratory oven at 200° F. The pretreated weight of the part was 13.3 grams, the wet weight of the part was 64.7 grams, and the dry weight of the part was 16.4 grams, i.e. a total add-on of 3.1 grams or 23% add-on.

The part was tested with a standard test procedure for cytotoxicity (NAMSA) and found to be non-toxic.

EXAMPLE 4

In this example, commercial quantities of silicone oil treated polyurethane parts were prepared by use of a heavy duty clothes washer and clothes dryer.

The carboxymethyl cellulose solution of Example 1 was prepared in corresponding ratios, but in a 55 gallon drum. The viscosity of that solution was 500 cp, as measured with a Brookfield viscometer.

Clean polyurethane foam parts were preweighed and tagged for identification purposes and placed in the washer basket until the basket was one-half full. The foam parts were then removed from the basket, and a portion of the carboxymethyl cellulose solution was transferred into the basket until the basket was approximately one-third full., The silicone oil of Example 1 was poured into the solution at the same ratio of Example 1 (the silicone oil had a Brookfield viscosity of 500 cp).

The washer was started and the silicone oil was allowed to mix with the carboxymethyl cellulose solution for about 3 minutes, at which time a dispersion of the silicone oil in the solution was obtained.

The foam parts were then placed in the basket and a "wash cycle" of about 5 minutes was allowed to take place so that the foam parts were thoroughly impregnated with the dispersion. The washer was allowed to then proceed through its spin cycle of about 2 minutes, and the washer was then stopped.

Ultrapure water was added to the basket such that the water covered the foam parts in the basket. The washer was reset to the "wash cycle", noted above, and run through that same cycle, for washing purposes. Thereafter, the washer was allowed to progress through the same spin cycle, and the washer was stopped.

A second wash as immediately described above was then performed with the ultrapure water, and after the spin cycle was completed, the foam parts were removed and placed in a conventional clothes dryer, which operates at an air temperature of about 145° F. The dryer was run for about 70 minutes, at which time the foam parts were dried and were removed from the dryer.

Each foam part was weighted and the add-ons of each foam part determined. While the add-on varied slightly from part to part, an average add-on of about 31% was achieved.

EXAMPLE 5

In this example, commercial-style equipment is used for producing the treated foam parts. The equipment is a Senco-Shop Star 501K machine.

A carboxymethyl cellulose solution having the ratios of Example 1 was prepared in one of the stainless steel tanks of the machine, and the Brookfield viscosity thereof was 500 cp.

Clean polyurethane foam parts were preweighed and tagged and loaded into the basked of the machine. Approximately 25 gallons of the carboxymethyl cellulose solution was transferred from the stainless steel tank to another empty stainless steel tank, and the ratioed amount of silicone oil of Example 1 was added thereto. By pumping that mixture between the two tanks, a dispersion of the silicone oil in the carboxymethyl cellulose solution was obtained.

Approximately 25 gallons of the dispersion was pumped to the basket and the foam parts added to the basket. The dispersion was pumped back and forth from the tank to the basket for about 5 minutes to treat the foam parts with the dispersion. Thereafter, the tank was drained of the dispersion, and about 15 gallons of ultrapure water was pumped into the basket. The basket was turned for 15 minutes, while recirculating the ultrapure water through the basket, foam parts, filters and back to the basket, for washing purposes. The water was then drained from the basket, and the remaining water was removed by high extract action of the basket for 4 minutes.

Thereafter, the dryer of the machine was turned on for 45 minutes at approximately 120° F., to dry the foam parts, and after drying, the foam parts were allowed to cool down for approximately 6 minutes. The foam parts were removed from the machine and post weighed. The add-ons were determined, and while there was some slight variation from part to part, the add-ons were approximately 32%.

It will be appreciated from the above that the present invention provides a novel, antifoam element, useful in a variety of applications, as well as processes for easily disposing silicone oil on a solid substrate, either in small lots, as may be used in small machines or for laboratory purposes, or in large lots, as may be used for large industrial processes. It will also be apparent from the foregoing that the invention admits to a number of modifications and variations, which would be clear to those skilled in the art from the above disclosure, and it is intended that those variations and modifications be included within the scope of the claims annexed hereto.

What is claimed is:

1. A method of adding an antifoam silicone oil to a solid substrate, comprising:

(A) mixing a silicone oil having a predetermined viscosity of at least about 100 cp and up to about 10,000 cp with an aqueous solution of one or more of a natural or synthetic water-soluble gum having a viscosity within about 20% of the predetermined viscosity of the silicone oil to form a dispersion of the silicone oil in the aqueous solution;

(B) contacting the substrate in the form of an antifoam element of a blood-handling apparatus with the dispersion so as to form a dispersion-wetted substrate; and (C) removing at least a part of the aqueous solution from the substrate, wherein the silicone oil remains in the substrate.

2. The method of claim 1 wherein the contacting is by one or more of immersion of the substrate in the dispersion, and spraying the substrate with the dispersion.

3. The method of claim 1 wherein the aqueous solution is removed from the substrate by one or more of centrifuging the substrate, applying a vacuum to the substrate, blowing onto the substrate a pressurized gas, displacing the aqueous solution with a water-insoluble fluid, dissolving the aqueous solution in an organic solvent and squeezing the substrate.

4. The method of claim 1 wherein after removing the aqueous solution, the substrate is dried.

5. The method of claim 1 wherein the amount of silicone oil added to the substrate is between about 0.5% and 50%.

6. The method of claim 1 wherein the amount of silicone oil in the dispersion is between about 0.1% and 8%.

7. The method of claim 6 wherein the amount of silicone oil in the dispersion is between about 1% and 5%.

8. The method of claim 1 wherein the silicone oil is a liquid at room temperature.

9. The method of claim 7 wherein the silicone oil has a viscosity from about 200 cp to about 3,000 cp.

10. The method of claim 1 wherein the viscosity of the aqueous solution is within about 15% of the predetermined viscosity of the silicone oil.

11. The method of claim 10 wherein the viscosity of the aqueous solution is within about 10% of the predetermined viscosity of the silicone oil.

12. The method of claim 1 wherein the water-soluble gum is one or more of carboxymethyl cellulose gum and polyacrylate gum.

13. The method of claim 1 wherein the substrate is porous.

14. The method of claim 13 wherein the substrate has at least in part hydrophobic surfaces.

15. The method of claim 14 wherein the substrate is an expanded surface substrate.

16. The method of claim 15 wherein the substrate is a foam.

17. The method of claim 16 wherein the foam is a polymeric foam.

18. The method of claim 17 wherein the foam is a polyurethane foam.

* * * * *